(12) United States Patent
Storey et al.

(10) Patent No.: US 7,049,289 B1
(45) Date of Patent: May 23, 2006

(54) LABELLED GLUTAMINE AND LYSINE ANALOGUES

(75) Inventors: Anthony Eamon Storey, Amersham (GB); Marivi Mendizabal, London (GB); Susan Champion, Chesham (GB); Alex Gibson, Little Chalfont (GB); Benedicte Guilbert, Rickmansworth (GB); Ian Andrew Wilson, Hitchin (GB); Peter Knox, Chalfont St. Giles (GB)

(73) Assignee: Amersham PLC, Buckinghamshire (GB)

( * ) Notice: Subject to any disclaimer, the term of this patent is extended or adjusted under 35 U.S.C. 154(b) by 0 days.

(21) Appl. No.: 09/674,616

(22) PCT Filed: May 14, 1999

(86) PCT No.: PCT/GB99/01550

§ 371 (c)(1),
(2), (4) Date: Dec. 19, 2000

(87) PCT Pub. No.: WO99/60018

PCT Pub. Date: Nov. 25, 1999

(30) Foreign Application Priority Data

May 15, 1998 (EP) ................................. 98303872

(51) Int. Cl.
*A61K 38/00* (2006.01)
(52) U.S. Cl. .......................................................... 514/9
(58) Field of Classification Search .................... 514/9
See application file for complete search history.

*Primary Examiner*—Christopher R. Tate
*Assistant Examiner*—Maury Audet
(74) *Attorney, Agent, or Firm*—Li Cai

(57) ABSTRACT

Synthetic analogues of lysine and glutamine are provided which function as substrates for the fibrin-stabilising enzyme Factor XIIIa even when labelled with a detectable moiety. The use of suitable protecting groups provides compounds which possess reduced susceptibility to in vivo metabolism especially by peptidases, and are hence useful agents for the diagnosis of thrombosis, embolism, atherosclerosis, inflammation or cancer.

10 Claims, 2 Drawing Sheets

Figure 1: Imaging with $^{99m}$Tc-Compound 5.
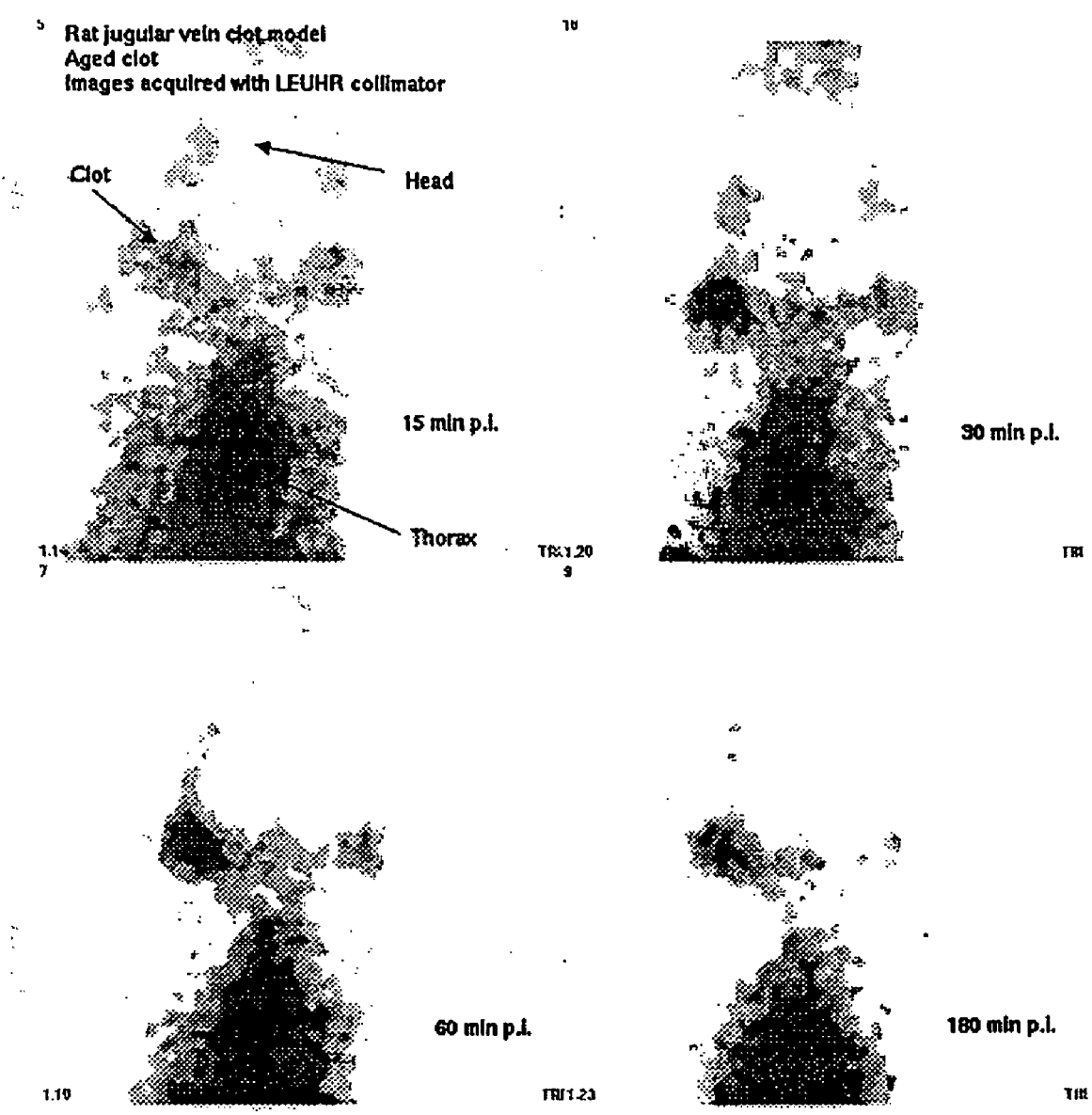

Figure 2: Imaging with $^{99m}$Tc-Compound 5.
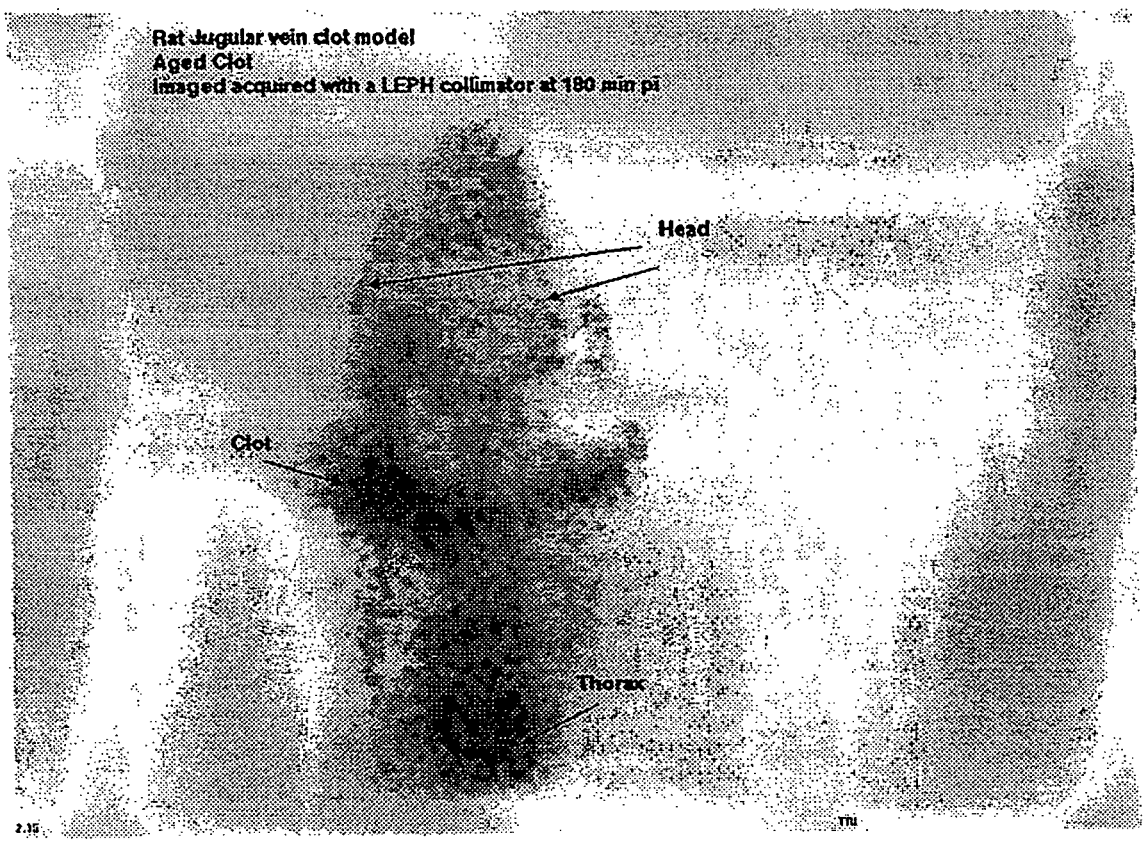

SEQUENCE LISTING

<160> NUMBER OF SEQ ID NOS: 38

<210> SEQ ID NO 1
<211> LENGTH: 12
<212> TYPE: PRT
<213> ORGANISM: Artificial Sequence
<220> FEATURE:
<223> OTHER INFORMATION: fragment of human antiplasmin

<400> SEQUENCE: 1

Asn Gln Glu Gln Val Ser Pro Tyr Thr Leu Leu Lys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: fragment of human antiplasmin
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 2

Asn Gln Glu Gln Val Ser Pro Tyr Thr Leu Leu Lys Gly
1               5                   10

<210> SEQ ID NO 3
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: BLOCKED

<400> SEQUENCE: 3

Asn Gln Glu Gln Val Ser Pro Tyr Thr Leu Leu Lys Gly
1               5                   10

<210> SEQ ID NO 4
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (13)..(13)
<223> OTHER INFORMATION: BLOCKED

<400> SEQUENCE: 4

Asn Gln Glu Gln Val Ser Pro Tyr Thr Leu Leu Lys Gly
1               5                   10

<210> SEQ ID NO 5
<211> LENGTH: 13

```
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (13)..(13)
<223> OTHER INFORMATION: BLOCKED

<400> SEQUENCE: 5

Asn Gln Glu Gln Val Ser Pro Tyr Thr Leu Leu Lys Gly
1               5                   10

<210> SEQ ID NO 6
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: BLOCKED

<400> SEQUENCE: 6

Asn Gln Glu Ala Val Ser Pro Tyr Thr Leu Leu Lys Gly
1               5                   10

<210> SEQ ID NO 7
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: BLOCKED

<400> SEQUENCE: 7

Asn Ala Glu Ala Val Ser Pro Tyr Thr Leu Leu Lys Gly
1               5                   10

<210> SEQ ID NO 8
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: BLOCKED

<400> SEQUENCE: 8

Asn Gln Gln Gln Val Ser Pro Tyr Thr Leu Leu Lys Gly
```

<210> SEQ ID NO 9
<211> LENGTH: 3
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: BLOCKED

<400> SEQUENCE: 9

Asn Gln Gly
1

<210> SEQ ID NO 10
<211> LENGTH: 6
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: BLOCKED

<400> SEQUENCE: 10

Asn Gln Glu Gln Val Gly
1               5

<210> SEQ ID NO 11
<211> LENGTH: 9
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (9)..(9)
<223> OTHER INFORMATION: BLOCKED

<400> SEQUENCE: 11

Asn Gln Glu Gln Val Ser Pro Tyr Gly
1               5

<210> SEQ ID NO 12
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)

```
<223> OTHER INFORMATION: BLOCKED

<400> SEQUENCE: 12

Asn Gln Glu Gln Val Ser Pro Leu Thr Leu Leu Lys Gly
1               5                   10

<210> SEQ ID NO 13
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (8)..(8)
<223> OTHER INFORMATION: MISC_FEATURE "Xaa" = 2-napthylalanine
<220> FEATURE:
<221> NAME/KEY: MOD_RES
<222> LOCATION: (13)..(13)
<223> OTHER INFORMATION: BLOCKED
<220> FEATURE:
<221> NAME/KEY: MOD_RES
<222> LOCATION: (1)..(1)
<223> OTHER INFORMATION: ACETYLATION

<400> SEQUENCE: 13

Asn Gln Glu Gln Val Ser Pro Xaa Thr Leu Leu Lys Gly
1               5                   10

<210> SEQ ID NO 14
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (8)..(8)
<223> OTHER INFORMATION: MISC_FEATURE "Xaa" = pBr-Phe
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: BLOCKED

<400> SEQUENCE: 14

Asn Gln Glu Gln Val Ser Pro Xaa Thr Leu Leu Lys Gly
1               5                   10

<210> SEQ ID NO 15
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (8)..(8)
<223> OTHER INFORMATION: MISC_FEATURE "Xaa" = I-Tyr
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: BLOCKED

<400> SEQUENCE: 15
```

```
Asn Gln Glu Gln Val Ser Pro Xaa Thr Leu Leu Lys Gly
1               5                   10
```

<210> SEQ ID NO 16
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (8)..(8)
<223> OTHER INFORMATION: MISC_FEATURE "Xaa" = diiodo-Tyr
<220> FEATURE:
<221> NAME/KEY: MOD_RES
<222> LOCATION: (13)..(13)
<223> OTHER INFORMATION: BLOCKED
<220> FEATURE:
<221> NAME/KEY: MOD_RES
<222> LOCATION: (1)..(1)
<223> OTHER INFORMATION: ACETYLATION

<400> SEQUENCE: 16

```
Asn Gln Glu Gln Val Ser Pro Xaa Thr Leu Leu Lys Gly
1               5                   10
```

<210> SEQ ID NO 17
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: BLOCKED
<220> FEATURE:
<221> NAME/KEY: MISC_FEATURE
<222> LOCATION: (8)..(8)
<223> OTHER INFORMATION: Xaa = iodo-tyrosine
<220> FEATURE:
<221> NAME/KEY: MOD_RES
<222> LOCATION: (13)..(13)
<223> OTHER INFORMATION: BLOCKED

<400> SEQUENCE: 17

```
Asn Gln Glu Gln Val Ser Pro Xaa Thr Leu Leu Lys Gly
1               5                   10
```

<210> SEQ ID NO 18
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: BLOCKED
<220> FEATURE:
<221> NAME/KEY: MISC_FEATURE
<222> LOCATION: (8)..(8)
<223> OTHER INFORMATION: Xaa = diiodo-Tyr
<220> FEATURE:
<221> NAME/KEY: MOD_RES
<222> LOCATION: (13)..(13)
<223> OTHER INFORMATION: BLOCKED

<400> SEQUENCE: 18

```
Asn Gln Glu Gln Val Ser Pro Xaa Thr Leu Leu Lys Gly
1               5                   10
```

```
<210> SEQ ID NO 19
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (12)..(12)
<223> OTHER INFORMATION: MISC_FEATURE "Xaa" = D-Lys
<220> FEATURE:
<221> NAME/KEY: MOD_RES
<222> LOCATION: (13)..(13)
<223> OTHER INFORMATION: BLOCKED
<220> FEATURE:
<221> NAME/KEY: MOD_RES
<222> LOCATION: (1)..(1)
<223> OTHER INFORMATION: ACETYLATION

<400> SEQUENCE: 19

Asn Gln Glu Gln Val Ser Pro Tyr Thr Leu Leu Xaa Gly
1               5                   10

<210> SEQ ID NO 20
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (8)..(8)
<223> OTHER INFORMATION: MISC_FEATURE "Xaa" = D-Tyr
<220> FEATURE:
<221> NAME/KEY: MOD_RES
<222> LOCATION: (13)..(13)
<223> OTHER INFORMATION: BLOCKED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (12)..(12)
<223> OTHER INFORMATION: MISC_FEATURE "Xaa" = D-Lys

<400> SEQUENCE: 20

Asn Gln Glu Gln Val Ser Pro Xaa Thr Leu Leu Xaa Gly
1               5                   10

<210> SEQ ID NO 21
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (6)..(6)
<223> OTHER INFORMATION: MISC_FEATURE "Xaa" = D-Ser
<220> FEATURE:
<221> NAME/KEY: MOD_RES
<222> LOCATION: (13)..(13)
<223> OTHER INFORMATION: BLOCKED
<220> FEATURE:
<221> NAME/KEY: MISC_FEATURE
<222> LOCATION: (8)..(8)
<223> OTHER INFORMATION: MISC_FEATURE "Xaa" = D-Tyr
<220> FEATURE:
<221> NAME/KEY: MISC_FEATURE
<222> LOCATION: (12)..(12)
<223> OTHER INFORMATION: MISC_FEATURE "Xaa" = D-Lys
<220> FEATURE:
<221> NAME/KEY: MOD_RES
<222> LOCATION: (1)..(1)
```

<223> OTHER INFORMATION: ACETYLATION

<400> SEQUENCE: 21

Asn Gln Glu Gln Val Xaa Pro Xaa Thr Leu Leu Xaa Gly
1               5                   10

<210> SEQ ID NO 22
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (5)..(5)
<223> OTHER INFORMATION: MISC_FEATURE"Xaa" = D-Val
<220> FEATURE:
<221> NAME/KEY: MOD_RES
<222> LOCATION: (13)..(13)
<223> OTHER INFORMATION: BLOCKED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: MISC_FEATURE "Xaa" = D-Ser
<220> FEATURE:
<221> NAME/KEY: MISC_FEATURE
<222> LOCATION: (8)..(8)
<223> OTHER INFORMATION: MISC_FEATURE "Xaa" = D-Tyr
<220> FEATURE:
<221> NAME/KEY: MISC_FEATURE
<222> LOCATION: (12)..(12)
<223> OTHER INFORMATION: MISC_FEATURE "Xaa" = D-Lys

<400> SEQUENCE: 22

Asn Gln Glu Gln Xaa Xaa Pro Xaa Thr Leu Leu Xaa Gly
1               5                   10

<210> SEQ ID NO 23
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (1)..(1)
<223> OTHER INFORMATION: MISC_FEATURE "Xaa" = D-Asn
<220> FEATURE:
<221> NAME/KEY: MOD_RES
<222> LOCATION: (13)..(13)
<223> OTHER INFORMATION: BLOCKED
<220> FEATURE:
<221> NAME/KEY: MISC_FEATURE
<222> LOCATION: (8)..(8)
<223> OTHER INFORMATION: MISC_FEATURE "Xaa" = D-Tyr
<220> FEATURE:
<221> NAME/KEY: MISC_FEATURE
<222> LOCATION: (12)..(12)
<223> OTHER INFORMATION: MISC_FEATURE "Xaa" = D-Lys
<220> FEATURE:
<221> NAME/KEY: MOD_RES
<222> LOCATION: (1)..(1)
<223> OTHER INFORMATION: ACETYLATION

<400> SEQUENCE: 23

Xaa Gln Glu Gln Val Ser Pro Xaa Thr Leu Leu Xaa Gly
1               5                   10

<210> SEQ ID NO 24

```
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (8)..(8)
<223> OTHER INFORMATION: MISC_FEATURE "Xaa" = D-Tyr
<220> FEATURE:
<221> NAME/KEY: MOD_RES
<222> LOCATION: (13)..(13)
<223> OTHER INFORMATION: bAla
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: BLOCKED
<220> FEATURE:
<221> NAME/KEY: MISC_FEATURE
<222> LOCATION: (12)..(12)
<223> OTHER INFORMATION: MISC_FEATURE "Xaa" = D-Lys

<400> SEQUENCE: 24

Asn Gln Glu Gln Val Ser Pro Xaa Thr Leu Leu Xaa Ala
1               5                   10

<210> SEQ ID NO 25
<211> LENGTH: 12
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (7)..(7)
<223> OTHER INFORMATION: MISC_FEATURE "Xaa" = D-Tyr
<220> FEATURE:
<221> NAME/KEY: MOD_RES
<222> LOCATION: (12)..(12)
<223> OTHER INFORMATION: BLOCKED
<220> FEATURE:
<221> NAME/KEY: MISC_FEATURE
<222> LOCATION: (11)..(11)
<223> OTHER INFORMATION: MISC_FEATURE "Xaa" = D-Lys
<220> FEATURE:
<221> NAME/KEY: MOD_RES
<222> LOCATION: (1)..(1)
<223> OTHER INFORMATION: BLOCKED

<400> SEQUENCE: 25

Gln Glu Gln Val Ser Pro Xaa Thr Leu Leu Xaa Gly
1               5                   10

<210> SEQ ID NO 26
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (5)..(12)
<223> OTHER INFORMATION: MISC_FEATURE = D-amino acids
<220> FEATURE:
<221> NAME/KEY: MOD_RES
<222> LOCATION: (13)..(13)
<223> OTHER INFORMATION: BLOCKED
<220> FEATURE:
<221> NAME/KEY: MOD_RES
<222> LOCATION: (1)..(1)
<223> OTHER INFORMATION: ACETYLATION
```

-continued

```
<400> SEQUENCE: 26

Asn Gln Glu Gln Val Ser Pro Tyr Thr Leu Leu Lys Gly
1               5                   10

<210> SEQ ID NO 27
<211> LENGTH: 9
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (2)..(9)
<223> OTHER INFORMATION: MISC_FEATURE = D-amino acids
<220> FEATURE:
<221> NAME/KEY: MOD_RES
<222> LOCATION: (9)..(9)
<223> OTHER INFORMATION: AMIDATION
<220> FEATURE:
<221> NAME/KEY: MOD_RES
<222> LOCATION: (1)..(1)
<223> OTHER INFORMATION: BLOCKED

<400> SEQUENCE: 27

Gly Lys Leu Leu Thr Tyr Pro Ser Val
1               5

<210> SEQ ID NO 28
<211> LENGTH: 9
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (5)..(5)
<223> OTHER INFORMATION: MISC_FEATURE "Xaa" = D-Val
<220> FEATURE:
<221> NAME/KEY: MOD_RES
<222> LOCATION: (9)..(9)
<223> OTHER INFORMATION: BLOCKED
<220> FEATURE:
<221> NAME/KEY: MISC_FEATURE
<222> LOCATION: (6)..(6)
<223> OTHER INFORMATION: MISC_FEATURE "Xaa" = O-methyl serine
<220> FEATURE:
<221> NAME/KEY: MOD_RES
<222> LOCATION: (1)..(1)
<223> OTHER INFORMATION: BLOCKED

<400> SEQUENCE: 28

Asn Gln Gln Gln Xaa Xaa Pro Leu Gly
1               5

<210> SEQ ID NO 29
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (13)..(13)
<223> OTHER INFORMATION: AMIDATION

<400> SEQUENCE: 29

Asn Gln Glu Gln Val Ser Pro Tyr Thr Leu Leu Lys Gly
```

```
<210> SEQ ID NO 30
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: BLOCKED

<400> SEQUENCE: 30

Asn Gln Glu Gln Val Ser Pro Tyr Thr Leu Leu Lys Gly
1               5                   10

<210> SEQ ID NO 31
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (13)..(13)
<223> OTHER INFORMATION: BLOCKED

<400> SEQUENCE: 31

Asn Gln Glu Gln Val Ser Pro Tyr Ala Ala Ala Ala Gly
1               5                   10

<210> SEQ ID NO 32
<211> LENGTH: 9
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (9)..(9)
<223> OTHER INFORMATION: BLOCKED

<400> SEQUENCE: 32

Asn Gln Glu Gln Val Ser Pro Tyr Gly
1               5

<210> SEQ ID NO 33
<211> LENGTH: 13
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (13)..(13)
<223> OTHER INFORMATION: Xaa = Gly which is cyclised with the Asn at
      residue 1
<220> FEATURE:
<221> NAME/KEY: MISC_FEATURE
```

```
<222> LOCATION: (1)..(1)
<223> OTHER INFORMATION: Xaa = Asn, which is cyclised with the Gly at
      residue 13

<400> SEQUENCE: 33

Xaa Gln Glu Gln Val Ser Pro Tyr Thr Leu Leu Lys Xaa
1               5                   10

<210> SEQ ID NO 34
<211> LENGTH: 10
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: BLOCKED

<400> SEQUENCE: 34

Leu Gly Pro Gly Gln Ser Lys Val Ile Gly
1               5                   10

<210> SEQ ID NO 35
<211> LENGTH: 6
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MISC_FEATURE
<222> LOCATION: (1)..(1)
<223> OTHER INFORMATION: MISC_FEATURE "Xaa" = pyro-Glu
<220> FEATURE:
<221> NAME/KEY: MOD_RES
<222> LOCATION: (6)..(6)
<223> OTHER INFORMATION: BLOCKED

<400> SEQUENCE: 35

Xaa Ala Gln Ile Val Gly
1               5

<210> SEQ ID NO 36
<211> LENGTH: 12
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: BLOCKED

<400> SEQUENCE: 36

Leu Glu Phe Asp Thr Gln Ser Lys Asn Ile Leu Gly
1               5                   10

<210> SEQ ID NO 37
<211> LENGTH: 7
<212> TYPE: PRT
<213> ORGANISM: Artificial Sequence
<220> FEATURE:
<223> OTHER INFORMATION: derivatised antiplasmin sequence
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: BLOCKED

<400> SEQUENCE: 37

Gly Gln Asp Pro Val Lys Gly
1               5

<210> SEQ ID NO 38
<211> LENGTH: 12
<212> TYPE: PRT
<213> ORGANISM: Artificial Sequence
<220> FEATURE:
<223> OTHER INFORMATION: derivatised antiplasmin sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: BLOCKED

<400> SEQUENCE: 38

Tyr Glu Val His His Gln Lys Leu Val Phe Phe Gly
1               5                   10
```

LABELLED GLUTAMINE AND LYSINE ANALOGUES

The present invention relates to a class of compounds useful in the diagnosis of sites of venous and arterial thrombosis, embolism or infection, pharmaceutical formulations containing them, their use in the diagnosis of disease and methods for their preparation.

Prior approaches to thrombus imaging radiopharmaceuticals include radiolabelled fibrinogen or plasminogen; radiolabelled fragment $E_1$ of human fibrin; radiolabelled plasminogen activators such as tissue plasminogen activator (t-PA) and labelled anti-fibrin antibodies. Methods based on the detection of sites of platelet accumulation such as the administration of radiolabelled platelets (e.g. using $^{111}$In oxine) or radiolabelled anti-platelet antibodies have also been described. More recent efforts have focused on radiolabelled peptides or polypeptides such as the cell adhesion motif RGD (where R, G and D are the standard abbreviations for the amino acids arginine, glycine and aspartic acid respectively); platelet factor 4 or fragments thereof or anti-coagulant peptides such as disintegrins.

Factor XIII is a plasma glycoprotein which is present in blood and certain tissues in a catalytically inactive (or zymogen) form. Factor XIII is transformed into its active form Factor XIIIa by thrombin in the presence of calcium ions. Factor XIIIa is also known as plasma transglutaminase, fibrinoligase or fibrin-stabilising factor. The final step in the formation of a blood clot is the covalent crosslinking of the fibrin which is formed by the proteolytic cleavage of fibrinogen by thrombin. Fibrin molecules align and the enzyme Factor XIIIa catalyses covalent crosslinking of the $NH_2$ and $CONH_2$ groups of lysyl and glutaminyl residues respectively giving structural rigidity to the blood clot. The crosslinking stabilises the fibrin clot structure and confers resistance to fibrinolysis. The crosslink formation is an important facet of normal blood coagulation and wound healing as well as pathological conditions such as thrombosis. As atherothrombotic brain infarctions are a common sub-type of stroke, Factor XIIIa substrates may allow diagnosis of stroke. It may also be implicated in atherosclerosis, inflammatory processes, tumour growth and metastasis. WO 91/16931 discloses that radiolabelled analogues of Factor XIII (in which the active site has been inactivated by amino acid substitution) are useful as thrombus imaging radiopharmaceuticals.

Factor XIIIa is also known to catalyse the incorporation of low molecular weight amines into the γ-glutamine sites of proteins. Similarly Factor XIIIa also catalyses the incorporation of low molecular weight glutamine analogues into lysyl residues. Thus such low molecular weight amines (or glutamine analogues) function as competitive inhibitors of the Factor XIIIa-induced lysyl/glutaminyl crosslinking of proteins. A range of synthetic amines have been described which are competitive inhibitors of the uptake of labelled putrescine (1,4-butanediamine) into N,N'-dimethylcasein catalysed by pig liver transglutaminase [L. Lorand et al., Biochem., 18, 1756(1979)].

WO 89/00051 (Cytrx Biopool Ltd.) claims a method for targeting fibrin deposits using a labelled compound which is covalently bound to fibrin by Factor XIIIa. The fibrin binding compound is stated to be "any peptide that is a substrate for the blood enzyme commonly known as Factor XIIIa". Preferred peptides are said to include the tetrapeptide sequence -Asn-Gln-Glu-Gln- (or NQEQ in standard amino acid abbreviation notation). Also disclosed is the 12-mer peptide sequence from the $NH_2$ terminus of the alpha-2 antiplasmin enzyme:
NH$_2$-Asn-Gln-Glu-Gln-Val-Ser-Pro-Leu-Thr-Leu-Thr-Leu-Leu-Lys-OH together with a synthetic analogue:
NH$_2$-Asn-Gln-Glu-Gln-Val-Ser-Pro-Tyr-Thr-Leu-Thr-Leu-Leu-Lys-OH, (denoted NQEQVSPLTLTLLK and NQEQVSPYTLTLLK respectively). The latter was radiolabelled with $^{125}$I and shown to be taken up in thrombin clots in vitro.

It has now been discovered that synthetic analogues of lysine and glutamine labelled with a suitable detectable moiety can also function as substrates for the enzyme Factor XIIIa. The use of suitable protecting groups provides compounds which are less susceptible to in vivo metabolism especially by peptidases, and are hence more useful targeting agents.

The present invention provides the following compounds:

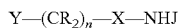

where:
X is C=O or $CR_2$;
n is an integer of value 1 to 6;
Y is $L(A)_m$— or $R^1R^2CR$— where L is a metal complexing agent, A is —$CR_2$—, —CR=CR—, —C≡C—, —NRCO—, —CONR—, —SO$_2$NR—, —NRSO$_2$—, —$CR_2OCR_2$—, —$CR_2SCR_2$—, —$CR_2NRCR_2$—, a $C_{4-8}$ cycloheteroalkylene group, a $C_{4-8}$ cycloalkylene group, a $C_{5-2}$ arylene group, a $C_{3-12}$ heteroarylene group or a polyalkyleneglycol, polylactic acid or polyglycolic acid moiety;
m is an integer of value 0 to 10;
where one of $R^1$ and $R^2$ is —$NH(B)_pZ^1$ and the other is —$CO(B)_qZ^2$ where
p and q are integers of value 0 to 45, and
each B is independently chosen from Q or an amino acid, where Q is a cyclic peptide;
$Z^1$ and $Z^2$ are protecting groups;
J and each R group are independently chosen from H, $C_{1-4}$ alkyl, $C_{1-4}$ alkenyl, $C_{1-4}$ alkynyl, $C_{1-4}$ alkoxyalkyl or $C_{1-4}$ hydroxyalkyl; with the provisos that:
(i) the total number of amino acid residues in the $R^1$ and $R^2$ groups does not exceed 45;
(ii) when X is $CR_2$, then Y is —$CRR^1R^2$ and $Z^2$ is a metal complexing agent;
(iii) when Y is —$CRR^1R^2$ then at least one of $R^1$ and $R^2$ bears at least one detectable moiety.

The invention also includes kits for the preparation of the above compounds labelled with a detectable moiety, and the use of these and related compounds in the diagnosis or therapy of thrombosis, embolism, atherosclerosis, inflammation or cancer.

By the term "cyclic peptide" is meant a sequence of 5 to 15 amino acids in which the two terminal amino acids are bonded together by a covalent bond which may be a peptide or disulphide bond or a synthetic non-peptide bond such as a thioether, phosphodiester, disiloxane or urethane bond.

By the term "amino acid" is meant an L- or D-amino acid, amino acid analogue or amino acid mimetic which may be naturally occurring or of purely synthetic origin, and may be optically pure, i.e. a single enantiomer and hence chiral, or a mixture of enantiomers. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles [see M. Goodman, Biopolymers, 24, 137, (1985)].

By the term "protecting group" is meant a biocompatible group which inhibits or suppresses in vivo metabolism of the peptide or amino acid at the amino or carboxyl terminus. Such groups are well known to those skilled in the art and are suitably chosen from, for the amine terminus ($Z^1$): acetyl, Boc (where Boc is tert-butyloxycarbonyl), Fmoc (where Fmoc is fluorenylmethoxycarbonyl), benzyloxycarbonyl, trifluoroacetyl, allyloxycarbonyl, Dde [i.e. 1-(4,4-dimethyl-2,6-dioxocyclohexylidene)ethyl], Npys (i.e. 3-nitro-2-pyridine sulfenyl), or a metal complexing group; and for the carboxyl terminus ($Z^2$): a carboxamide, tert-butyl ester, benzyl ester, cyclohexyl ester, amino alcohol or a metal complexing group. Preferably the protecting group is a metal complexing group, most preferably it is a metal complexing group bound to a metal i.e. a metal complex. The carboxyl terminus of peptides is particularly susceptible to in vivo cleavage by carboxypeptidase enzymes. Consequently, the metal complexing group or metal complex is preferably attached at the carboxyl terminus. When either $R^1$ is —NH(B)$_{p-1}$QZ$^1$ or $R^2$ is —CO(B)$_{q-1}$QZ$^2$ then the protecting group may be the covalent bond which closes the cyclic peptide (O) ring.

A "detectable moiety" is a moiety which emits a signal or is suitable for diagnostic imaging of the human body and may be a radioisotope for radiopharmaceutical imaging or therapy, a paramagnetic metal or species for MRI contrast imaging, a radiopaque group or metal for X-ray contrast imaging, a gas microbubble ultrasound contrast agent or a suitable dye for detection by external light imaging. Preferably, the imaging moiety is a metal ion, most preferably it is a radiometal.

When Y is —CRR$^1$R$^2$, then preferably either one or both of $R^1$ and $R^2$ comprises one or more peptide fragments of $\alpha_2$-antiplasmin, fibronectin or beta-casein, fibrinogen or thrombospondin. Such peptide fragments comprise at least 3 and preferably 4–20 amino acid residues. When Y is —CRR$^1$R$^2$ and —(CR$_2$)—X—NHJ is —(CH$_2$)$_4$NH$_2$ (i.e. the amino acid side chain of lysine), then preferably either one or both of $R^1$ and $R^2$ comprises one or more such peptide fragments of $\alpha_2$-antiplasmin, fibronectin or beta-casein. The amino acid sequences of $\alpha_2$-antiplasmin, fibronectin, beta-casein, fibrinogen and thrombospondin can be found in the following references: $\alpha_2$-antiplasmin precursor [M. Tone et al., J. Biochem, 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al., Proc. Natl. Acad. Sci., USA, 83, 5449, (1986)]; R. F. Doolittle, Ann. Rev. Biochem., 53, 195, (1984).

Preferably the amino acid sequence is taken from the N-terminus of:

(i) $\alpha_2$-antiplasmin, i.e. NH$_2$-Asn-Gln-Glu-Gln-Val-Ser-Pro-Leu-Thr-Leu-Thr-Leu-Leu-Lys-OH or variants of this in which one or more amino acids have been exchanged, added or removed such as:

NH$_2$-Asn-Gln-Glu-Gln-Val-Ser-Pro-Leu-Thr-Leu-Thr-Leu-Leu-Lys-Gly-OH,

NH$_2$-Asn-Gln-Glu-Ala-Val-Ser-Pro-Leu-Thr-Leu-Thr-Leu-Leu-Lys-Gly-OH,

NH$_2$-Asn-Gln-Glu-Gln-Val-Gly-OH; or (ii) casein ie. Ac-Leu-Gly-Pro-Gly-Gln-Ser-Lys-Val-Ile-Gly.

When the compound of the present invention is a peptide, i.e. Y is R$^1$R$^2$CR— the number of amino acid residues is preferably 2 to 30, most preferably 3 to 20, especially 3 to 15.

Preferred compounds have J equal H, i.e. terminate in an NH$_2$ group. X is preferably C=O, i.e. compounds of formula Y—(CR$_2$)$_n$—CONH$_2$ are preferred. Most preferred compounds are of formula Y—(CR$_2$)$_y$—(CH$_2$)$_2$CONH$_2$ or Y—(CR$_2$)$_y$—(CH$_2$)$_4$NH$_2$ where x is an integer of value 0 to 4, and y is an integer of value 0 to 3. Compounds having the same side chain as glutamine, i.e. glutamine analogues of formula Y—(CR$_2$)$_x$—(CH$_2$)$_2$CONH$_2$ are especially preferred.

Suitable non-metallic radioisotopes for use in the present invention include but are not limited to: radioiodine such as $^{123}$I, $^{125}$I, $^{131}$I, preferably $^{123}$I; positron emitters such as $^{18}$F, $^{11}$C or $^{75}$Br and isotopes for therapy e.g. $^{211}$At.

The compounds of this invention which comprise metal complexing agents preferably have only a single type of targeting molecule attached, i.e. the —(CR$_2$)$_n$—X—NHJ substituent. Other substituents on the complexing agent may be present, but the —(CR$_2$)$_n$—X—NHJ substituent is the one which is expected to be primarily responsible for the biolocalisation properties. Metal complexes of the present invention may contain one or more metal ions which may be the same or different. Thus in some circumstances polynuclear complexes may have advantageous properties such as certain metal clusters which have superparamagnetic properties and are hence particularly useful as MRI contrast agents. Preferred metal complexes of the present invention involve only a single metal ion. When the metal of the metal complex is a radiometal, it can be either a positron emitter (such as $^{68}$Ga or 64Cu) or a γ-emitter such as $^{99m}$Tc, $^{111}$In, $^{111}$In or $^{67}$Ga. Suitable metal ions for use in MRI are paramagnetic metal ions such as gadolinium(III) or manganese(II). Most preferred radiometals for diagnostic imaging are γ-emitters, especially $^{99m}$Tc. Metal complexes of certain radionuclides may be useful as radiopharmaceuticals for the radiotherapy of various diseases such as cancer or the treatment of thrombosis or restenosis. Useful radioisotopes for such radiotherapeutic applications include: $^{90}$Y, $^{89}$Sr, $^{67}$Cu, $^{186}$Re, $^{88}$Re, $^{169}$Er, $^{153}$Sm and $^{198}$Au. Whichever metal complex is chosen, it is strongly preferred that it is bound to the Factor XIIIa substrate in such a way that it does not undergo facile metabolism in blood with the result that the metal complex is cleaved from the Factor XIIIa substrate before the labelled Factor XIIIa substrate reaches the desired in vivo site to be imaged. The Factor XIIIa substrate is therefore preferably covalently bound to the metal complexes of the present invention.

These metal ions are complexed using a metal complexing agent, or more preferably a chelating agent. The chelating agents comprise 2–10 metal donor atoms covalently linked together by a non-coordinating backbone. Preferred chelating agents have 4–8 metal donor atoms and have the metal donor atoms in either an open chain or macrocyclic arrangement or combinations thereof. Most preferred chelating agents have 4–6 metal donor atoms and form 5- or 6-membered chelate rings when coordinated to the metal centre. Such polydentate and/or macrocyclic chelating agents form stable metal complexes which can survive challenge by endogenous competing ligands for the metal in vivo such as transferrin or plasma proteins. Alternatively, it is possible to use monodentate complexing agents that form stable complexes with the desired metal ion even though they do not form chelate rings upon metal coordination. Examples of known complexing agents of this kind, which are particularly suitable for use with $^{99m}$Tc, are hydrazines, phosphines, arsines, or isonitriles.

Examples of suitable chelating agents are bidentate such as diamines or diphosphines, tridentate such as monoaminedithiols, or tetradentate such as diaminedioximes (U.S. Pat. No. 4,615,876) or such ligands incorporating amide donors (WO 94/08949); the tetradentate ligands of WO 94/22816; N$_2$S$_2$ diaminedithiols, diamidedithiols or amideaminedithiols; N$_3$S thioltriamides; N$_4$ ligands such as tetraamines, macrocyclic amine or amide ligands such as cyclam, oxocyclam (which forms a neutral technetium complex) or dioxocyclam; or dithiosemicarbazones. The above described ligands are particularly suitable for technetium, but are useful for other metals also. Other suitable ligands are described in Sandoz WO 91/01144, which includes ligands which are particularly suitable for indium, yttrium and gadolinium, especially macrocyclic aminocarboxylate and aminophosphonic acid ligands. Ligands which form non-ionic (i.e. neutral) metal complexes of gadolinium are known and are described in U.S. Pat. No. 4,885,363. The ligand may also comprise a short sequence of amino acids such as the Cys/amino acid/Cys tripeptide of WO 92/13572 or the peptide ligands described in EP 0719790 A2.

Preferred chelating agents have the formula

where each a is 2 or 3
each b is 1 or 2
one R is aminoalkylene through which the chelating agent is joined to the rest of the molecule
each other R is independently H, $C_1$–$C_{10}$ hydrocarbyl, alkoxy, alkoxyalkyl, amine, amide, hydroxyl, hydroxyalkyl or carboxylate or two R groups taken together with the atoms to which they are attached form a carboxylic, heterocyclic saturated or unsaturated ring.

Non-peptide-based metal chelating agents provide improved control over attachment and release of metal ions, and are preferred.

The invention also includes a peptide fragment of $\alpha_2$-antiplasmin, fibronectin, beta-casein, tetanus, amyloid, trappin or polyglutamine, said peptide fragment containing 3–45 amino acid residues and carrying a terminal metal complexing agent.

It is well known to prepare chelating agents which have attached thereto a functional group ("bifunctional chelates"). Functional groups which have been attached to chelating agents include: amine, carboxylic acid, cyanate, thiocyanate, maleimide and active ester such as N-hydroxysuccinimide. Examples of chelate-amine conjugates for diaminedioxime ligands are given in WO 95/19187. When the desired Factor XIIIa substrate functionality is an amine, the ligands of the present invention can be prepared by reaction of a bifunctional compound which contains both an amine group (preferably protected by use of suitable protecting groups known to those skilled in the art), and a reactive group such as a sulphonyl chloride, acid chloride, active ester or an alkyl/benzyl halide. The reactive group can then be coupled to either the pendant amine group of a bifunctional chelate, or used to derivatise one or more of the amine donor atoms of a N-containing ligand. Alternatively, a monoprotected diamine could be reacted with a bifunctional chelate with a pendant active ester or carboxyl group to give the protected amine group linked to the ligand system via an amide bond. In both synthetic routes outlined above, the resulting ligand-protected amine conjugate is then deprotected under suitable conditions to give the desired amine-functionalised ligand. When the desired Factor XIIIa substrate functionality is a carboxamide group, the desired ligands can be prepared e.g. by reaction of a omega-haloalkyl carboxamide of suitable chain length with a bifunctional chelate with a pendant amine group, giving the desired carboxamide-linked ligand.

The metal complexes of the present invention may be prepared by reacting a solution of the metal in the appropriate oxidation state with the ligand at the appropriate pH. The solution may preferably contain a ligand which complexes weakly to the metal (such as chloride, gluconate or citrate) i.e. the metal complex is prepared by ligand exchange or transchelation. Such conditions are useful to suppress undesirable side reactions such as hydrolysis of the metal ion. When the metal ion is $^{99m}$Tc, the usual starting material is sodium pertechnetate from a $^{99}$Mo generator. Technetium is present in $^{99m}$Tc-pertechnetate in the Tc(VII) oxidation state, which is relatively unreactive. The preparation of technetium complexes of lower oxidation state Tc(I) to Tc(V) therefore usually requires the addition of a suitable reducing agent such as stannous ion to facilitate complexation. Further suitable reductants are described below.

The metal complex should also preferably exhibit low non-specific blood background.

Thus the present invention relates mainly to diagnostic agents for imaging sites in the mammalian body where the enzyme Factor XIII is activated and blood proteins such as fibrin or collagen are deposited. The present agents are particularly useful for the diagnostic imaging of the human body. The agents comprise substrates for the enzyme Factor XIIIa which are labelled with a metal complex suitable for external imaging such as a radiometal (for scintigraphy) or a paramagnetic metal ion (for MRI). The metal complex of the present invention has a pendant amino or carboxamide functional group which is available for covalent linking to protein glutamyl carboxamide or lysyl amine groups respectively by the enzyme Factor XIIIa. The intimate relationship of fibrin and Factor XIIIa highlights the potential use of the agents of the present invention for the diagnosis of disease states where there is both fibrin deposition or accumulation and activation of Factor XIII. Increased fibrin deposition is known to be characteristic of diseases such as thrombosis, atherosclerosis, fibrotic liver, and disseminated intravascular coagulation. Fibrin is also deposited at sites of tissue inflammation associated with many disease processes, such as infection, autoimmune disease or cancer. Factor XIII and tissue transglutaminase are activated during known physiological conditions. During apoptosis and generation of new matrix protein structures elevated levels of the enzymes are seen. The present agents may thus also be used for the detection of apoptosis and diseases states such as arthritis where increased matrix protein deposition occurs. Since Factor XIII is activated at the site of interest in vivo (i.e. thrombus, embolism etc.) this provides a localisation mechanism for the metal complexes of the present invention. The covalently linked metal complexes can then be imaged externally by radionuclide scintigraphy or magnetic resonance imaging (MRI) hence providing a non-invasive means of diagnosing the disease site.

So far as the therapeutic aspects of this invention are concerned, the inventors have preliminary in vivo data (not reported in detail herein) indicating that clots produced in the presence of labelled peptides of the present invention (as per Example 17 below) are smaller than those produced in the absence of the labelled peptide. On this basis it is proposed that the peptides herein defined, typically containing 4–30 e.g. about 10 amino acid residues, are effective as drugs for increasing the rate of clot lysis e.g. by acting as potent inhibitors of fibrin cross linking in clots. Thus the compounds disclosed have possible pharmaceutical uses as thrombolytic or anticoagulant drugs for therapy.

The present invention also relates to kits for the preparation of metal complexes linked to Factor XIIIa substrates. The kits are designed to give sterile products suitable for human administration, e.g. via injection into the bloodstream. Possible embodiments are discussed below. When the detectable moiety is $^{99m}$Tc, the kit would comprise a vial containing the free ligand or chelating agent for the metal together with a pharmaceutically acceptable reducing agent such as sodium dithionite, sodium bisulphite, ascorbic acid, formamidine sulphinic acid, stannous ion, Fe(II) or Cu(I), preferably a stannous salt such as stannous chloride or stannous tartrate. Alternatively, the kit could contain a metal complex which, upon addition of the radiometal or paramagnetic metal, undergoes transmetallation (i.e. ligand exchange) giving the desired product. For $^{99m}$Tc, the kit is preferably lyophilised and is designed to be reconstituted with sterile $^{99m}$Tc-pertechnetate (TcO$_4$ from a $^{99m}$Tc radio-isotope generator to give a solution suitable for human administration without further manipulation.

The agents of the present invention may also be provided in a unit dose form ready for human injection and could for example be supplied in a pre-filled sterile syringe. When the detectable moiety is a radioactive isotope such as $^{99m}$Tc, the syringe containing the unit dose would also be supplied within a syringe shield (to protect the operator from potential radioactive dose).

The above kits or pre-filled syringes may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid) or bulking agents for lyophilisation (such as sodium chloride or mannitol).

The following examples illustrate the preparation of compounds of the present invention and their use in imaging. The syntheses of particular compounds of the present invention are given in Examples 1–9, their radiolabelling with 123I or $^{99m}$Tc in Examples 10–12. Compound 1 (prior art) is included as a comparative example. Evidence for increased plasma stability in vitro is given in Example 13. Evidence for uptake in blood clots in vitro and in vivo is given in Examples 15 and 17 respectively, with normal rat biodistribution of the radiolabelled compounds reported in Example 16.

The in vitro plasma stability of $^{123}$I-Compound 1 is poor (see Example 13), presumably due to protease activity. The introduction of protecting groups at both the carboxy and amino termini as for radiolabelled Compounds 2–5 and 7–49 confers a substantial increase in plasma stability.

The majority of compounds tested exhibit high in vitro clot uptake and hence avidity for the clot. The other compounds are of lower potency with compounds 14, 16, 18, 31, 34, 36, 46 and 48 showing significant reduction in uptake. Removal of the Gln residue from position 2 of the a$_2$-antiplasmin derived sequences, as in compound 14, causes a large drop in uptake of this tracer, thus strongly suggesting that Gln-2 is an essential amino acid in this sequence type.

Details of the biodistribution in normal rats and in the fresh and aged clot models are given in Examples 16 and 17. The blood clearance rate of these compounds is relatively fast with biological half lives between 1–2 hours. The biodistribution of $^{99m}$Tc-Compound 3 is given as a representative example, in this case the $t_{1/2}$ of 2 h is estimated. The rapid clearance from background tissues such as blood, lung, heart and muscle shows that the agent of the present invention possess favourable pharmacokinetics for imaging and shows their potential as radiodiagnostics. Although some hepatobiliary excretion is seen for these compounds, the main route of excretion is via the urinary tract.

Uptake into fresh and aged clots in the rat models for many of the radiolabelled compounds is very good (relative concentration or RC=5–15), with clot to background tissue ratios very favourable for imaging (>5). Example 18 shows that $^{99m}$Tc-Compound 5 is suitable for imaging clots in the rat model.

$^{99m}$Tc-Compounds 2–49 have improved plasma stability compared with $^{123}$I-Compound 1 (RC=1.5), which may be responsible for the improved in vivo clot uptake seen with these compounds.

Comparison of the clot uptake results of Example 17 for fresh and aged clots, shows that the present agents exhibit uptake which is constant and independent of the age of the clot. Thus such agents will have improved imaging capability for pre-existing clots, such as those found with pulmonary embolism.

DETAILED DESCRIPTION OF THE DRAWINGS

FIG. 1: Imaging of clots induced in a rat model with $^{99m}$Tc-Compound 5. Images shown were acquired at 15 min p.i., 30 min p.i., 60 min p.i., and 180 min p.i.

FIG. 2: Imaging of clots induced in a rat model with $^{99m}$Tc-Compound 5: detailed image at 180 min p.i.

EXPERIMENTAL

In the following table:

Z is benzyloxycarbonyl,

Fmoc is fluorenylmethoxycarbonyl,

Ac is acetyl,

Pn44 ius

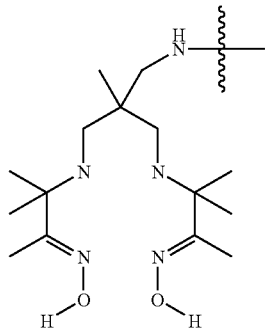

Pn216 is

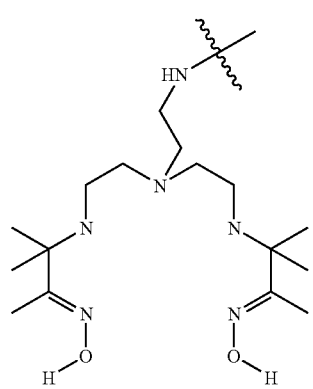

Hynic is

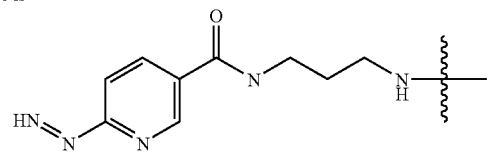

| Peptide | Compound | MS Theor. | MS Expt. |
|---|---|---|---|
| NQEQVSPYTLLK | 1 | 1419.6 | 1419.7[a] |
| Ac-NQEQVSPYTLLKG-NH$_2$ | 2 | 1517.7 | 1517.7 |
| Ac-NQEQVSPYTLLKG-Pn44 | 3 | 1816.1 | 1816.2 |
| Ac-NQEQVSPYTLLKG-Hynic | 4 | 1709.7 | 1710.0 |
| Ac-NQEQVSPYTLLKG-Pn216 | 5 | 1845.2 | 1845.2 |
| NQEQVSPYTLLKG-Pn216 | 6 | 1803.1 | 1803.3 |
| Z-NQEQVSPYTLLKG-Pn44 | 7 | 1908.2 | 1908.1 |
| Z-NQEQVSPYTLLKG-Pn216 | 8 | 1937.2 | 1937.2 |
| Fmoc-NQEQVSPYTLLKG-Pn216 | 9 | 2025.4 | 2025.4 |
| (CF$_3$)$_2$(C$_6$H$_3$)-NQEQVSPYTLLKG-Pn216 | 10 | 2044.2 | 2045.2 |
| Adamantoyl-NQEQVSPYTLLKG-Pn216 | 11 | 1966.0 | 1966.5 |
| Ac-NQEAVSPYTLLKG-Pn44 | 12 | 1759.1 | 1759.0 |
| Ac-NQEAVSPYTLLKG-Pn216 | 13 | 1788.1 | 1788.0 |
| Ac-NAEAVSPYTLLKG-Pn216 | 14 | 1766.1 | 1765.8 |
| Ac-NQQQVSPYTLLKG-Pn216 | 15 | 1844.2 | 1844.1 |
| Ac-NQG-Pn44 | 16 | 656.8 | 656.6 |
| Ac-NQEQVG-Pn44 | 17 | 1908.2 | 1908.1 |
| Z-NQEQVSPYG-Pn216 | 18 | 1481.7 | 1481.7 |
| Ac-NQEQVSPLTLLKG-Pn216 | 19 | 1795.2 | 1795.1 |
| Ac-NQEQVSP-Nal(2)-TLLKG-Pn216 | 20 | 1879.3 | 1879.3 |
| Ac-NQEQVSP(pBr-F)TLLKG-Pn216 | 21 | 1908.1 | 1908.9 |
| Ac-NQEQVSP(I-Y)TLLKG-Pn216 | 22 | 1971.2 | 1972.4 |
| Ac-NQEQVSP(I$_2$-Y)TLLKG-Pn216 | 23 | 2098.2 | 2099.5 |
| Z-NQEQVSP(I-Y)TLLKG-Pn216 | 24 | 2063.2 | 2064.4 |
| Z-NQEQVSP(I$_2$-Y)TLLKG-Pn216 | 25 | 2189.2 | 2190.5 |
| Fmoc-NQEQVSP(I-Y)TLLKG-Pn216 | 26 | 2152.4 | 2153.4 |
| Fmoc-NQEQVSP(I$_2$-Y)TLLKG-Pn216 | 27 | 2278.4 | 2279.3 |
| Ac-NQEQVSPYTLL(D-K)G-Pn216 | 28 | 1845.2 | 1845.2 |
| Ac-NQEQVSP(D-Y)TLL(D-K)G-Pn216 | 29 | 1845.2 | 1845.1 |
| Ac-NQEQV(D-S)P(D-Y)TLL(D-K)G-Pn216 | 30 | 1845.2 | 1845.2 |
| Ac-NQEQ(D-V)(D-S)P(D-Y)TLL(D-K)G-Pn216 | 31 | 1845.2 | 1845.1 |
| Ac-(D-N)QEQVSP(D-Y)TLL(D-K)G-Pn216 | 32 | 1845.2 | 1845.0 |
| Ac-NQEQVSP(D-Y)TLL(D-K)βAla-Pn216 | 33 | 1859.2 | 1859.0 |
| Ac-N—CH$_2$NH$_2$-QEQVSP(D-Y)TLL(D-K)G-Pn216 | 34 | 1831.2 | 1831.1 |
| Ac-NQEQ(D-V)(D-S)(D-P)(D-Y)(D-T)(D-L)(D-L)(D-K)G-Pn44 | 35 | 1816.1 | 1815.8 |
| Pn216-CO(CH$_2$)$_3$CO-G(D-K)(D-L)(D-L)(D-T)(D-Y)(D-P)(D-S)(D-V)NH$_2$ | 36 | 1916.2 | 1916.0 |
| Fmoc-NQQQ(D-V)S(OMe)PLG-Pn216 | 37 | 1532.8 | 1532.7 |
| Pn44-CO(CH$_2$)$_3$CO-NQEQVSPYTLLKG-NH$_2$ | 38 | 1887.7 | 1887.3 |
| Pn216-CO(CH$_2$)$_3$CO-NQEQVSPYTLLKG-NH$_2$ | 39 | 1916.2 | 1916.3 |
| Ac-NQEQVSPYTLLKG-(PEG)$_{3.4k}$-Pn44 | 40 | 5200–5600 | 5401[b] |
| Ac-NQEQVSPYTLLKG-(PEG)$_{10k}$-Pn216 | 41 | 12400- | 12630[b] |
| Z-NQEQVSPYAAAAG-Pn216 | 42 | 1766.0 | 1765.9 |
| Z-NQEQVSPYG(CH$_2$)$_{11}$(CO)-Pn216 | 43 | 1677.7 | 1679.8 |
| Cyclo-[NQEQVSPYTLLKG] | 44 | 1458.6 | 1458.3 |
| Ac-LGPGQSKVIG-Pn44 | 45 | 1294.6 | 1294.4 |
| p-EAQIVG-Pn44 | 46 | 1023.2 | 1023.0 |
| Ac-LEFDTQSKNILG-Pn216 | 47 | 1733.0 | 1732.9 |
| Ac-GQDPVKG-Pn216 | 48 | 1068.3 | 1068.0 |
| Ac-YEVHHQKLVFFG-Pn216 | 49 | 1872.2 | 1872.3 |

All compounds except those denoted were analysed using ES+ mass spectrometry. Those compounds denoted by [a] were analysed by FAB and [b] by MALDI-TOF mass spectrometry.

Example 1

Syntheses of Compounds 1 and 2

The protected peptide Ac-Asn(Trt)-Gln(Trt)-Glu(OtBu)-Gln(Trt)-Val-Ser(tBu)-Pro-Tyr(tBu)-Thr(tBu)-Leu-Leu-LYs(Boc)-Gly-OH was assembled on a 2-chlorotrityl resin by anchoring Fmoc-Lys(Boc) to the resin, and then successive deprotections/coupling cycles with the appropriate protected amino acids (as described in P. Lloyd-Williams, F. Albericio and E. Girald; *Chemical Approaches to the Synthesis of Peptides and Proteins*, CRC Press, 1997). The title compound was obtained by cleavage using 0.1% TFA in dichloromethane, deprotection and purification by RP-HPLC (System A).

Example 2

Syntheses of Compounds 3–9, 12–21, 28–33, 35, 37, 42 and 45–49

The appropriate protected peptide was assembled as in Example 1 with the appropriate protected amino acids. The protected fragment was cleaved from the resin and then coupled with 6-aminomethyl-3,3,6,9,9-pentamethyl-4,8-diazaundecane-2,10-dione dioxime (prepared as described in WO 95119187), 3,3,11,11-tetramethyl-7-aminoethyl-4,7,10-triazatridecane-2,12-dionedioxime (prepared as described in WO 98/31399) or 6Boc-hydrazinopyridine-3-carboxylic acid N-hydroxysuccinimide ester (prepared as described in U.S. Pat. No. 5,206,370) in solution using BOP as a coupling agent. The title compounds were obtained by

Example 3

Syntheses of Compounds 22–27

In an Eppendorf vial compound 5, 8 or 9 (1 mg), ammonium acetate buffer (400 µl, 0.2M, pH4), sodium iodide (0.5 eq, 15 mg/10 ml in 0.1M NaOH) and peracetc acid (1.5 eq, 0.1M solution) were added. The reaction mixture was thoroughly mixed for 1 minute and the mono- and di-iodo products were separated and collected by preparative HPLC. The procedure was repeated to give sufficient quantities of the isolated products.

Example 4

Syntheses of Compounds 10 and 11

Fmoc-Asn(Trt)-Gln(Trt)-Glu(tBu)-Gln(Trt)-Val-Ser(tBu)-Pro-Tyr(tBu)-Thr(tBu)-Leu-Leu-Lys(Boc)-Gly (200 mg, 0.73 mmol), Pn216 (30 mg, 0.87 mmol) and HBTU (33 mg, 0.87 mmol) were dissolved in anhydrous DMF (2.5 ml). To the solution was added diisopropylethylamine (20 ml, 1.15 mmol) and the reaction mixture was stirred at room for 1.75 hours. The reaction mixture was then treated with piperidine (0.5 ml) and the mixture stirred at room temperature for 2 hours. The product was purified by semi-preparative HPLC to give a white solid (171 mg, 82%); ES$^+$-MS: m/z 952.40 (M+3H$^+$).

1-Adamantanecarboxylic acid or 3,5-bis(trifluoromethyl) benzoic acid (1.5 molar equivalent), the protected peptide Asn(Trt)-Gln(Trt)-Glu(tBu)-Gln(Trt)-Val-Ser(tBu)-Pro-Tyr(tBu)-Thr(tBu)-Leu-Leu-Lys(Boc)-Gly-Pn216 (1 molar equivalent) and HBTU (1.2–1.5 molar equivalent) were dissolved in anhydrous DMF (1 ml). Diisopropylethylamine (11 molar equivalents) was added and the reaction mixture was stirred at room temperature until the reaction was judged complete by HPLC. The protected peptide fragment was then treated with 95% trifluoroacetic acid in $CH_2Cl_2$. The reaction mixture was stirred at room temperature for 2 to 4 hrs. The product was purified from the reaction mixture by reversed phase HPLC.

Example 5

Synthesis of Compound 34

The protected peptide was synthesised as for example 1 with the exception of the Fmoc-Asn(Trt)-Ψ(CH$_2$NH)-Gln(Trt)-OH which was obtained according to the classical methodology for the synthesis of reduced peptide bonds, by reductive amination of Gln(Trt) with Fmoc-Asn(Trt) derived aldehyde (see G. Guichard et al., *Peptide Res.*, 6(3), 121, (1993) and references therein.

The resulting compound was prepared and purified as in example 2.

Example 6

Syntheses of Compounds 36, 38 and 39

The protected peptide was synthesised as for example 1 but 10 on a Rink resin. After removal of the glycine N-protection, the peptide was reacted with glutaric anhydride whilst still on the resin. Activation with BOP/HOBt of the glutarate carboxylic acid and coupling with 6-aminomethyl-3,3,6,9,9-pentamethyl-4,8-diazaundecane-2,10-dione dioxime or 3,3,11,11-tetramethyl-7-aminoethyl-4,7, 10-triazatridecane-2, 12-dionedioxime on the resin gave the protected product. Cleavage with TFA/water (95/5) afforded the crude material which was purified using RP-HPLC (System A).

Example 7

Syntheses of Compounds 40 and 41

A solution of the required molecular weight α-N-(tert-butoxycarbonyl)-poly(ethylene glycol) amino-ω-succinimidyl carbonate and one molar equivalent of 6-aminomethyl-3,3,6,9,9-pentamethyl-4,8-diazaundecane-2,10-dione dioxime or 3,3,11,11-tetramethyl-7-aminoethyl-4,7,10-triazatridecane-2,12-dionedioxime in anhydrous tetrahydrofuran (5 ml) was refluxed for 5 hours under nitrogen. The reaction mixture was reduced in vacuo leading to a white solid which was purified by flash chromatography using isopropanol/ammonia/water 10:1:1 to give the title compound as a white solid. The Boc protecting group was removed using 37% HCl added dropwise to an ice-cold solution in methanol. The solution was then stirred at room temperature for 4 hours. The reaction mixture was basified to pH~10 by addition of 4M NaOH (4.18 ml). The product was isolated by semi-preparative HPLC (system D).

The solid from above was dissolved in DMF and to it was added the protected peptide fragment. Diisopropylethylamine and HBTU were added and the reaction mixture was stirred at room temperature till completion of the reaction. The product was purified by HPLC (system E) to give a colourless gum.

This gum was dissolved in dichloromethane (2 ml) and the solution treated with TFA (0.2 ml) for 5 hours. The reaction was basified with 1M NaOH (2 ml) and volatiles removed in vacuo. MeOH (2.5 ml) was added to the residue and the mixture filtered using an Acrodisc filter (LC13 PVDF 0.45 m). The product was isolated from the methanolic solution by HPLC (system E).

Example 8

Synthesis of Compound 43

12-N-Fmoc-aminododecanoic acid was coupled to ,3,11,11-tetramethyl-7-aminoethyl-4,7,10-triazatridecane-2,12-dionedioxime as described earlier. The Fmoc protecting group was removed by 20% piperidine in DMF and the product purified by HPLC (system F).

The above product was coupled with the protected peptide fragment and subsequently deprotected as described above. The product was purified by HPLC (system G).

Example 9

Synthesis of Compound 44

The partially deprotected peptide H-Asn(Trt)-Gln(Trt)-Glu(OtBu)-Gln(Trt)-Val-Ser(tBu)-Pro-Tyr(tBu)-Leu-Leu-Lys(Boc)-Gly-OH was assembled on a 2-chlorotrtyl chloride resin, by a Fmoc based strategy, by stepwise elongation with BOP/HOBt. The N-terminal protection was removed by piperidine treatment and partially protected peptide cleaved from the solid support by a 0.5% TFA in dichloromethane solution.

Cyclisation was carried out in solution at a 10 mM concentration in DMF, with BOP as a condensation reagent, in the presence of solid sodium bicarbonate according to a known methodology (see for instance M. Rodriguez et al., *Int J. Pept. Protein Res.*, 35, 441, 1990).

Final deprotection in a mixture of TFA/water/ethane dithiol (90/5/5) afforded the crude title compound which was purified by RP-HPLC (System A).

Example 10

I-123 Labelling of Compounds 1–2 and Compound 44

Ammonium acetate buffer (200 µl, 0.2M, pH 4.0) was added to the ligand solution (20 µl, 20 µg), and $Na^{127}I$ (10 µl, 1.5 µg) in an Eppendorf tube. The solution was mixed thoroughly and $Na^{123}I$ (5–50 µl, 111 MBq) was then added. The solution was mixed thoroughly prior to addition of PAA solution (10 µl 0.01M), further mixing followed. The activity of the preparation was measured. In all cases the required product was separated from reaction by-products and unlabelled substrates by HPLC.

Example 11

Tc-99m Labelling of Compounds 3, 5–43, 45–49

A 0.1 ml aliquot of the compound dissolved in $H_2O$ (1 mg/ml) was transferred to a nitrogen-filled 10 ml glass vial together with deoxygenated saline (0.9% w/v, 1 ml) and 0.035 ml aqueous NaOH (0.1M). To this solution was added technetium generator eluate (1 ml, approx. 0.4 GBq) and then aqueous stannous chloride solution (0.1 ml, ca. 10 µg). The labelling pH was 9.0–10.0. Vials were incubated at ambient laboratory temperature (15–25° C.) for 30 minutes to effect labelling. The resulting preparation was either diluted to the desired radioactive concentration or HPLC purification was performed (System B) to remove unlabelled starting material and radioactive impurities prior to testing. After purification the organic solvent was removed under vacuum and the sample was redissolved in about 5 ml 0.1M phosphate buffer pH 7.4 to give a working concentration of 6–9 MBq/ml. Radiochemical purity was assessed before use by the thin layer chromatography (TLC) system described below:

i) ITLC SG 2 cm×20 cm eluted with 0.9% w/v saline
ii) Whatman No. 1 2 cm×20 cm eluted with 50:50 v/v acetonitrile: $H_2O$ The labelled substrates remain at, or close to, the origin in TLC system (i) and move close to the solvent front in system (ii). When analysed by appropriate detection equipment the radiochemical purity is typically in excess of 85% labelled compound.

Example 12

Tc-99m Labelling of Compound 4

A 0.1 ml aliquot of the compound dissolved in water (1 mg/ml) was transferred to nitrogen-filled 10 ml glass vial together with tricine dissolved in water (0.5 ml, 37.5 mg) and phosphinedynetris(benzene sulphonic acid)tris sodium salt dissolved in water (0.1 ml, 10 mg). To this solution was added technetium generator eluate (1 ml, approx 0.4 GBq) and then a solution of stannous chloride in 0.1M HCl (0.02 ml, ca 2 µg). The labelling pH was 4.5–5.5. Vials were incubated at 60° C. for 30 minutes to effect labelling. Purification and assessment of radiochemical purity was carried out as in Example 10.

Example 13

In Vitro Plasma Stability

To a portion of compound (50 µl, 10 MBq/ml) was added an equal volume of plasma (rat or human) or saline. The mixtures were incubated at 37° C. and the stability measured by HPLC (system C) at 0, 30 and 120 minutes. The saline dilution acted as a control.

| Compound | Species | % intact at 120 mins |
|---|---|---|
| $^{123}I$-Cmpd 1 (prior art) | Human | 0 |
| $^{123}I$-Cmpd 2 | Human | 98 |
|  | Rat | 99 |
| $^{99m}Tc$-Cmpds 3, 4, 5, 7, 12, 16, 17; $^{123}I$-Cmpd 44 | Human | >90 |
|  | Rat | >90 |
| $^{99m}Tc$-Cmpds 8-11, 13–15, 19–21, 28–36, 38, 39, 45–49 | Rat | >90 |
| $^{99m}Tc$-Cmpds 22–27 | Rat | >60 |

Example 14

HPLC Systems

| Flow Rate: | 1 ml/min in all systems. |
|---|---|

System A

| Column | Waters C18 250 × 4.5 mm. Particle size 4 microns |
|---|---|
| Gradient: | Elution Profile 10–60% B in 25 min. |
| Eluent A: | 0.1% aqueous TFA |
| Eluent B: | 0.1% TFA in acetonitrile |

System B

| Column | Waters C18 150 × 3.9 mm. Particle size 4 microns |
|---|---|
| Gradient: | Elution Profile 0–100% B in 22 min. |
| Eluent A: | 0.1% aqueous TFA |
| Eluent B: | 0.1% TFA in acetonitrile |

System C

| Column | Waters C18 150 × 3.9 mm. Particle size 4 microns |
|---|---|
| Gradient: | Elution Profile 0–100% B in 20 min. |
| Eluent A: | 50 mM $NH_4OAc$ buffer (pH 5.6) |
| Eluent B: | acetonitrile |

System D

| | |
|---|---|
| Column | Hamilton PRP-1, 305 mm × 7.0 mm; |
| Gradient: | Elution Profile 0–65% B in 10 min. |
| Eluent A: | 5% aqueous ammonia |
| Eluent B: | acetonitrile |

System E

| | |
|---|---|
| Column | Hamilton PRP-1, 150 mm × 4.1 mm; |
| Gradient: | Elution Profile 0–100% B in 15 min. |
| Eluent A: | 5% aqueous ammonia |
| Eluent B: | acetonitrile |

System F

| | |
|---|---|
| Column | Polymer Laboratories PLRP-S, 150 mm × 2.5 mm; |
| Gradient: | Elution Profile 0–100% B in 15 min. |
| Eluent A: | 5% aqueous ammonia |
| Eluent B: | acetonitrile |

System G

| | |
|---|---|
| Column | Hamilton PRP-1, 150 mm × 4.1 mm; |
| Gradient: | Elution Profile 0–100% B in 15 min. |
| Eluent A: | 0.1% aqueous TFA |
| Eluent B: | 0.1% TFA in acetonitrile |

Example 15

Incorporation into Human Plasma Clots

Incorporation of radiolabelled substrates into fibrin was investigated by induction of an in vitro human plasma clot in the following manner. To a siliconised 5 ml glass vial was added, (a) 800 μl of Tris(hydroxymethyl)aminomethane buffered saline pH 7.5 containing calcium chloride (50 mM Tris, 150 mM sodium chloride, 4 mM calcium chloride.), (b) about 40 μl of physiological salt solution containing 100 units of thrombin per ml, (c) about 400 μl of human plasma containing the radiolabelled substrate at a concentration of typically 10 kBq/ml. To aid induction of clot a roughened glass rod was added to the reaction vial. Control vials were prepared similarly but with the omission of thrombin and calcium chloride.

After incubation of the test solution at ambient laboratory temperature (ca. 20° C.) for 60 minutes the reaction was discontinued with the addition of about 400 μl of a cold solution of 33.5 mM ethylenediaminetetra-acetic acid disodium salt. Clots were separated from serum by vacuum filtration onto 0.45 μM nitrocellulose filters (pre-soaked in 1.5% BSA/tris(hydroxymethyl)aminoethae buffered saline pH 7.5 containing 0.1% Tween 20) and washed with about 2×10 ml of tris(hydroxymethyl)aminomethane buffered saline pH 7.5 containing Tween 20 to a final concentration of 0.1% v/v. The proportion of total radioactivity was calculated by counting in suitable detection apparatus.

The fraction of radioactivity retained on the filter, after subtraction of the non-specific binding determined from the control, is a measure of incorporation into the filtered clots.

| Compound | % retained (with thrombin) | % retained (no thrombin) | % specific uptake* |
|---|---|---|---|
| $^{123}$I-Cmpd 1 | 14.6 | 2.0 | 12.6 |
| $^{123}$I-Cmpd 2 | 38.6 | 0.2 | 38.4 |
| $^{99m}$Tc-Cmpd 3 | 39.3 | 0.3 | 39.0 |
| $^{99m}$Tc-Cmpd 4 | 22.0 | 0.1 | 21.0 |
| $^{99m}$Tc-Cmpd 5 | 35.5 | 0.2 | 35.3 |
| $^{99m}$Tc-Cmpd 6 | 68.6 | 4.3 | 64.3 |
| $^{99m}$Tc-Cmpd 7 | 41.3 | 0.7 | 40.6 |
| $^{99m}$Tc-Cmpd 8 | 25.9 | 1.4 | 24.5 |
| $^{99m}$Tc-Cmpd 9 | 44.5 | 2.7 | 42.8 |
| $^{99m}$Tc-Cmpd 10 | 65.9 | 0.2 | 65.7 |
| $^{99m}$Tc-Cmpd 11 | 68.1 | 1.2 | 66.9 |
| $^{99m}$Tc-Cmpd 12 | 34.8 | 0.3 | 34.5 |
| $^{99m}$Tc-Cmpd 13 | 57.0 | 0.2 | 56.8 |
| $^{99m}$Tc-Cmpd 14 | 3.3 | 0.5 | 2.8 |
| $^{99m}$Tc-Cmpd 15 | 55.6 | 0.4 | 55.2 |
| $^{99m}$Tc-Cmpd 16 | 12.5 | 0.1 | 12.4 |
| $^{99m}$Tc-Cmpd 17 | 41.3 | 0.7 | 40.6 |
| $^{99m}$Tc-Cmpd 18 | 9.8 | 0.1 | 9.7 |
| $^{99m}$Tc-Cmpd 19 | 48.2 | 0.2 | 48.0 |
| $^{99m}$Tc-Cmpd 20 | 65.0 | 2.6 | 62.4 |
| $^{99m}$Tc-Cmpd 21 | 60.6 | 0.5 | 60.1 |
| $^{99m}$Tc-Cmpd 22 | 59.0 | 0.3 | 58.7 |
| $^{99m}$Tc-Cmpd 23 | 63.8 | 0.1 | 63.7 |
| $^{99m}$Tc-Cmpd 24 | 56.8 | 0.4 | 56.4 |
| $^{99m}$Tc-Cmpd 25 | 68.0 | 4.3 | 63.7 |
| $^{99m}$Tc-Cmpd 26 | 63.3 | 8.2 | 55.1 |
| $^{99m}$Tc-Cmpd 27 | Nd | Nd | nd |
| $^{99m}$Tc-Cmpd 28 | 42.1 | 0.2 | 41.9 |
| $^{99m}$Tc-Cmpd 29 | 21.1 | 0.1 | 21.0 |
| $^{99m}$Tc-Cmpd 30 | 14.9 | 0.2 | 14.7 |
| $^{99m}$Tc-Cmpd 31 | 7.7 | 0.1 | 7.6 |
| $^{99m}$Tc-Cmpd 32 | 20.2 | 0.4 | 19.8 |
| $^{99m}$Tc-Cmpd 33 | 63.9 | 0.1 | 63.8 |
| $^{99m}$Tc-Cmpd 34 | 5.5 | 0.1 | 5.4 |
| $^{99m}$Tc-Cmpd 35 | 15.9 | 0.6 | 15.3 |
| $^{99m}$Tc-Cmpd 36 | 8.7 | 0.1 | 8.6 |
| $^{99m}$Tc-Cmpd 37 | 13.0 | 0.2 | 12.8 |
| $^{99m}$Tc-Cmpd 38 | 21.0 | 0.7 | 20.3 |
| $^{99m}$Tc-Cmpd 39 | 23.1 | 0.1 | 23.0 |
| $^{99m}$Tc-Cmpd 40 | 13.3 | 0.1 | 13.2 |
| $^{99m}$Tc-Cmpd 41 | 44.5 | 7.1 | 37.4 |
| $^{99m}$Tc-Cmpd 42 | 14.2 | 0.2 | 14.0 |
| $^{99m}$Tc-Cmpd 43 | | | |
| $^{123}$I-Cmpd 44 | 14.1 | 0.3 | 13.8 |
| $^{99m}$Tc-Cmpd 45 | 28.7 | 0.1 | 28.6 |
| $^{99m}$Tc-Cmpd 46 | 6.3 | 0.2 | 6.1 |
| $^{99m}$Tc-Cmpd 47 | 49.9 | 0.1 | 49.8 |
| $^{99m}$Tc-Cmpd 48 | 10.6 | 0.1 | 10.5 |
| $^{99m}$Tc-Cmpd 49 | 33.1 | 1.6 | 31.5 |

*% retained in plasma clot assay (with thrombin) - % retained in plasma clot assay (no thrombin)

Example 16

Normal Rat Biodistribution

The resolution of a clot image is dependant on the combination of rate of incorporation of the radiopharmaceutical and its blood/tissues clearance rate. For this reason the biodistribution of several compounds has been determined in rats. Male Wistar (100–150 g) rats were injected i.v. with 0.1–0.2 ml of radiolabelled tracer solution (8 MBq/ml) and dissected at different times post-injection. The % ID in each of the selected tissues was measured. Some animals were kept in metabolism cages to be able to determine the % ID excreted in urine and faeces. The dissection times used for the agent were 15, 30, 60, 240 min. Data are shown as mean of % ID (n=3).

$^{99m}$Tc-Compound 3

|  | 15 min | 30 min | 60 min | 240 min |
|---|---|---|---|---|
| Muscle | 14.7 | 10.4 | 5.1 | 2.9 |
| Blood | 5.3 | 1.8 | 1.6 | 0.6 |
| Kidney | 7.6 | 4.9 | 4.6 | 3.4 |
| Urine | 14.9 | 34.3 | 37.0 | 42.0 |
| Lung | 0.7 | 0.4 | 0.3 | 0.3 |
| Liver | 6.2 | 4.1 | 4.0 | 3.0 |
| GI Tract | 13.5 | 15.1 | 18.0 | 20.7 |
| Heart | 0.2 | 0.1 | 0.1 | 0.04 |

Example 17

Incorporation into Clots Induced in a Rat Model

Rat Inferior Vena Cava Model (IVC)

The rats (Male Wistar, 250–350 g) were anaesthetised with 15% urethane. After laparotomy, the vena cava was isolated and freed of surrounding fat tissue. A platinum wire (1.5 cm×0.5 mm) was inserted into the inferior vena cava and 5 min post surgery 0.4 ml of ellagic acid ($1.2 \times 10^{-4}$ M) was injected intravenously through the femoral vein previously canulated, and the clot was allowed to form. The average weight of the clots formed in this model was around 27 mg, n=32, (5–50 mg range). The compounds were injected 5 min (fresh clot) and 60 min (aged clot) post-induction. After 60 min the animals were sacrificed and the clot removed, weighed and counted. Other tissues e.g. blood, lung, heart, were also dissected and counted. The uptake of tracer into the clot was determined as the relative concentration (cpm/g of clot by dose/g animal) and clot to background tissue.

Results:

| | | Fresh Clots | | | | |
|---|---|---|---|---|---|---|
| Compound | % id/g | Rel. Conc. | Clot/ blood | Clot/ lung | Clot/ heart | Clot/ liver |
| $^{123}$I-Cmpd 1 | 0.5 ± 0.1 | 1.6 ± 0.4 | 1 | nd | Nd | nd |
| $^{123}$I-Cmpd 2 | 4.9 ± 0.8 | 14.5 ± 2.2 | 7 | 10 | 19 | 21 |
| $^{99m}$Tc-Cmpd 3 | 1.4 ± 0.4 | 5.1 ± 1.2 | 10 | 8 | 17 | 6 |
| $^{99m}$Tc-Cmpd 4 | 2.0 ± 0.6 | 6.5 ± 2.0 | 6 | 8 | 15 | 20 |
| $^{99m}$Tc-Cmpd 5 | 6.0 ± 2.1 | 16 ± 5.8 | 21 | 23 | 51 | 43 |
| $^{99m}$Tc-Cmpd 7 | 4.8 ± 1.3 | 14.5 ± 4.4 | 15 | 11 | 21 | 6 |
| $^{99m}$Tc-Cmpd 8 | 6.7 ± 1.7 | 21.0 ± 6.8 | 14 | 18 | 41 | 21 |
| $^{99m}$Tc-Cmpd 9 | 8.8 ± 3.6 | 24.8 ± 9.6 | 13 | 12 | 32 | 13 |
| $^{99m}$Tc-Cmpd 10 | 2.9 ± 0.5 | 6.5 ± 1.2 | 4 | 5 | 10 | 5 |
| $^{99m}$Tc-Cmpd 11 | 1.1 ± 0.4 | 3.3 ± 1.1 | 10 | 11 | 24 | 11 |
| $^{99m}$Tc-Cmpd 12 | 7.3 ± 4.1 | 19.8 ± 11.0 | 20 | 17 | 31 | 8 |
| $^{99m}$Tc-Cmpd 13 | 3.4 ± 0.7 | 7.9 ± 1.6 | 7 | 8 | 18 | 18 |
| $^{99m}$Tc-Cmpd 14 | 0.5 ± 0.1 | 1.2 ± 0.2 | 2 | 1.5 | 3 | 0.7 |
| $^{99m}$Tc-Cmpd 15 | 3.6 ± 1.0 | 8.3 ± 2.2 | 4 | 6 | 12 | 11 |
| $^{99m}$Tc-Cmpd 16 | 0.3 ± 0.1 | 1.0 ± 0.2 | 3 | 3 | 8 | 0.8 |
| $^{99m}$Tc-Cmpd 17 | 1.2 ± 0.7 | 3.7 ± 2.3 | 7 | 12 | 18 | 5 |
| $^{99m}$Tc-Cmpd 19 | 2.5 ± 0.3 | 7.1 ± 1.2 | 3 | 7 | 29 | 17 |
| $^{99m}$Tc-Cmpd 20 | 2.3 ± 0.6 | 6.5 ± 1.3 | 12 | 11 | 30 | 18 |
| $^{99m}$Tc-Cmpd 21 | 2.3 ± 1.3 | 7.4 ± 4.0 | 11 | 16 | 28 | 13 |
| $^{99m}$Tc-Cmpd 22 | 3.8 ± 1.6 | 13.0 ± 5.5 | 11 | 13 | 28 | 25 |
| $^{99m}$Tc-Cmpd 23 | 7.6 ± 1.8 | 18.2 ± 4.1 | 6 | 6 | 17 | 21 |
| $^{99m}$Tc-Cmpd 24 | 4.0 ± 2.2 | 11.1 ± 6.7 | 10 | 10 | 21 | 11 |
| $^{99m}$Tc-Cmpd 26 | 14.1 ± 10 | 41.4 ± 28 | 16 | 11 | 38 | 16 |
| $^{99m}$Tc-Cmpd 28 | 3.5 ± 2.0 | 9.7 ± 5.0 | 13 | 19 | 31 | 35 |
| $^{99m}$Tc-Cmpd 29 | 4.7 ± 1.9 | 13.0 ± 4.9 | 14 | 20 | 44 | 44 |
| $^{99m}$Tc-Cmpd 31 | 0.3 ± 0.2 | 0.9 ± 0.6 | 0.6 | 1 | 2 | 3 |
| $^{99m}$Tc-Cmpd 32 | 1.7 ± 0.7 | 4.6 ± 1.9 | 10 | 11 | 26 | 27 |
| $^{99m}$Tc-Cmpd 33 | 2.7 ± 0.2 | 7.8 ± 0.6 | 11 | 16 | 32 | 28 |
| $^{99m}$Tc-Cmpd 34 | 0.5 ± 0.2 | 1.8 ± 0.5 | 2 | 3 | 6 | 8 |
| $^{99m}$Tc-Cmpd 35 | 1.2 ± 0.2 | 3.7 ± 0.8 | 2 | 2 | 4 | 2 |
| $^{99m}$Tc-Cmpd 36 | 0.2 ± 0.1 | 0.7 ± 0.3 | 1 | 1 | 3 | 4 |
| $^{99m}$Tc-Cmpd 37 | 0.4 ± 0.2 | 0.9 ± 0.4 | 0.6 | 0.7 | 1 | 1 |
| $^{99m}$Tc-Cmpd 38 | 1.9 ± 0.5 | 5.4 ± 1.5 | 5 | 6 | 15 | 3 |
| $^{99m}$Tc-Cmpd 39 | 2.5 ± 0.3 | 9.0 ± 1.1 | 9 | 14 | 29 | 31 |
| $^{99m}$Tc-Cmpd 41 | 0.7 ± 0.1 | 2.2 ± 0.3 | 3 | 4 | 6 | 8 |
| $^{99m}$Tc-Cmpd 42 | 0.3 ± 0.1 | 0.3 ± 0.2 | 2 | 0.3 | 1 | 63 |
| $^{123}$I-Cmpd 44 | 0.4 ± 0.1 | 1.1 ± 0.2 | 0.9 | 1.5 | 1 | 2 |
| $^{99m}$Tc-Cmpd 45 | 2.0 ± 0.5 | 5.5 ± 1.3 | 6 | 5 | 10 | 3 |
| $^{99m}$Tc-Cmpd 46 | 0.8 ± 0.4 | 2.0 ± 0.7 | 5 | 3 | 6 | 1 |
| $^{99m}$Tc-Cmpd 47 | 0.8 ± 0.7 | 2.2 ± 2.0 | 0.8 | 1 | 3 | 1 |
| $^{99m}$Tc-Cmpd 48 | 0.3 ± 0.2 | 1.0 ± 0.5 | 0.6 | 0.9 | 2 | 3 |
| $^{99m}$Tc-Cmpd 49 | 2.6 ± 1.1 | 8.5 ± 3.7 | 4 | 6 | 16 | 4 |

$$\text{Rel. Conc.(RC)} = \frac{\% \text{ id/g of clot}}{\% \text{ id/g in rest of body}}$$

| Aged Clots | | | | | | |
|---|---|---|---|---|---|---|
| Compound | % id/g | Rel. Conc. | Clot/blood | Clot/lung | Clot/heart | Clot/liver |
| $^{123}$I-Cmpd 2 | 5.5 ± 1.7 | 14.5 ± 3.9 | 24 | 12 | 23 | 20 |
| $^{99m}$Tc-Cmpd 3 | 2.1 ± 0.8 | 6.2 ± 2.2 | 8 | 11 | 23 | 5 |
| $^{99m}$Tc-Cmpd 4 | 1.2 ± 1.1 | 4.1 ± 4.0 | 8 | 10 | 19 | 19 |
| $^{99m}$Tc-Cmpd 5 | 3.6 ± 1.7 | 11 ± 5.1 | 13 | 31 | 33 | 24 |
| $^{99m}$Tc-Cmpd 7 | 2.1 ± 0.3 | 6.5 ± 1.3 | 9 | 7 | 15 | 3 |
| $^{99m}$Tc-Cmpd 8 | 5.3 ± 1.3 | 16.4 ± 4.3 | 10 | 9 | 24 | 16 |
| $^{99m}$Tc-Cmpd 9 | 3.7 ± 0.4 | 11.4 ± 1.5 | 8 | 7 | 21 | 6 |
| $^{99m}$Tc-Cmpd 10 | 2.9 ± 1.4 | 6.3 ± 2.7 | 6 | 6 | 16 | 5 |
| $^{99m}$Tc-Cmpd 11 | 0.4 ± 0.3 | 1.2 ± 0.8 | 5 | 6 | 13 | 4 |
| $^{99m}$Tc-Cmpd 12 | 4.1 ± 1.2 | 11.2 ± 3.4 | 19 | 15 | 75 | 7 |
| $^{99m}$Tc-Cmpd 13 | 4.5 ± 1.5 | 10.4 ± 3.0 | 6 | 9 | 29 | 19 |
| $^{99m}$Tc-Cmpd 14 | 0.6 ± 0.4 | 1.4 ± 0.8 | 1.4 | 1.3 | 2 | 0.7 |
| $^{99m}$Tc-Cmpd 15 | 3.4 ± 0.6 | 7.6 ± 1.6 | 3 | 0.6 | 1 | nd |
| $^{99m}$Tc-Cmpd 17 | 0.8 ± 0.1 | 2.7 ± 0.6 | 3 | 5 | 7 | 3 |
| $^{99m}$Tc-Cmpd 19 | 3.2 ± 2.3 | 9.1 ± 7.1 | 14 | 5 | 13 | 6 |
| $^{99m}$Tc-Cmpd 20 | 1.7 ± 0.5 | 4.9 ± 1.4 | 10 | 14 | 36 | 23 |
| $^{99m}$Tc-Cmpd 21 | 2.7 ± 2.3 | 8.5 ± 6.8 | 31 | 13 | 32 | 31 |
| $^{99m}$Tc-Cmpd 22 | 6.9 ± 2.5 | 22.7 ± 7.4 | 11 | 1 | 3 | 4 |
| $^{99m}$Tc-Cmpd 23 | 7.5 ± 2.5 | 17.6 ± 4.6 | 13 | 1 | 1 | 1 |
| $^{99m}$Tc-Cmpd 24 | 4.1 ± 2.5 | 11.9 ± 8.0 | 15 | 20 | 40 | 37 |
| $^{99m}$Tc-Cmpd 26 | 4.0 ± 0.9 | 12.9 ± 3.5 | 7 | 12 | 31 | 54 |
| $^{99m}$Tc-Cmpd 28 | 4.5 ± 1.1 | 13.1 ± 3.4 | 17 | 2 | 3 | 1 |
| $^{99m}$Tc-Cmpd 29 | 3.8 ± 0.4 | 10.0 ± 1.7 | 11 | 30 | 67 | 29 |
| $^{99m}$Tc-Cmpd 31 | 0.2 ± 0.1 | 0.6 ± 0.2 | 0.6 | 4 | 9 | 2 |
| $^{99m}$Tc-Cmpd 32 | 0.7 ± 0.1 | 2.0 ± 0.4 | 3 | 15 | 43 | 21 |
| $^{99m}$Tc-Cmpd 33 | 2.2 ± 0.6 | 6.7 ± 1.6 | 16 | 9 | 24 | 16 |
| $^{99m}$Tc-Cmpd 34 | 0.4 ± 0.1 | 1.4 ± 0.4 | 3 | — | — | 6 |
| $^{99m}$Tc-Cmpd 35 | 0.6 ± 0.1 | 1.5 ± 0.4 | 1 | 0.5 | 1 | 2 |
| $^{99m}$Tc-Cmpd 36 | 0.1 ± 0.02 | 0.2 ± 0.1 | 0.6 | 10 | 18 | 4 |
| $^{99m}$Tc-Cmpd 37 | 0.2 ± 0.03 | 0.5 ± 0.1 | 0.4 | 1 | 2 | 9 |
| $^{99m}$Tc-Cmpd 38 | 0.8 ± 0.3 | 2.4 ± 0.7 | 3 | 0.5 | 1 | 2 |
| $^{99m}$Tc-Cmpd 39 | 2.4 ± 0.3 | 8.2 ± 1.1 | 15 | 12 | 43 | 11 |
| $^{99m}$Tc-Cmpd 41 | 0.4 ± 0.1 | 1.1 ± 0.3 | 1 | 6 | 13 | 4 |
| $^{99m}$Tc-Cmpd 42 | 0.4 ± 0.1 | 1.3 ± 0.3 | 5 | 7 | 21 | 6 |
| $^{123}$I-Cmpd 44 | 0.5 ± 0.03 | 1.2 ± 0.1 | 0.9 | 2 | 1 | 1 |
| $^{99m}$Tc-Cmpd 45 | 2.0 ± 0.8 | 5.7 ± 2.3 | 8 | 5 | 11 | 3 |
| $^{99m}$Tc-Cmpd 46 | 0.5 ± 0.2 | 1.3 ± 0.6 | 4 | 3 | 5 | 1 |
| $^{99m}$Tc-Cmpd 47 | 0.5 ± 0.3 | 1.5 ± 0.8 | 1 | 24 | 46 | 44 |
| $^{99m}$Tc-Cmpd 48 | 0.2 ± 0.04 | 0.8 ± 0.2 | 1 | 109 | 32 | 26 |
| $^{99m}$Tc-Cmpd 49 | 1.2 ± 0.5 | 3.9 ± 1.6 | 4 | 9 | 29 | 19 |

Example 18

Imaging of Clots Induced in a Rat Model

Clots were induced in male Wistar rats (250–350 g) as described in Example 17, with the exception that for these experiments the platinum wire was located in the jugular vein. The compounds were injected 60 min post injection and planar images acquired between 15–180 min p.i. A Park medical Isocam I gamma camera was used for these experiments, 300K or 150K counts were of the thorax were collected using a LEUHR or a LEPH collimator. Clots were visualised from 15 min p.i. Reaching the highest clot to background ratio at 180 min p.i. due to rapid clearance of the compound.

Abbreviations

| | |
|---|---|
| Ac | Acetyl |
| Boc | tert-butyloxycarbonyl |
| Cmpd | compound |
| DMF | dimethylformamide |
| ES | electrospray |
| FAB | fast atom bombardment |
| Fmoc | fluorenylmethoxycarbonyl |
| HPLC | high performance liquid chromatography |
| MALDI-TOF | matrix assisted laser desorption ionisation - time of flight |
| Nal | napthylalanine |
| RCP | radiochemical purity |
| RP-HPLC | reverse phase high performance liquid chromatography |
| TFA | trifluoroacetic acid |
| TLC | thin layer chromatography |

What is claimed is:

1. A compound of formula:

$$Y-(CR_2)_n X-NHJ$$

where:
- X is C=O or $CR_2$;
- n is an integer of value 1 to 6;
- Y is $R^1R^2CR-$ where one of $R^1$ and $R^2$ is $-NH(B)_pZ^1$ and the other is $-CO(B)_qZ^2$ where
- p and q are integers of value 0 to 30, and
- each B is independently chosen from Q or an amino acid residue,
- where Q is a cyclic peptide;
- $Z^1$ and $Z^2$ are metal complexing agents (L) or other protecting groups, which are biocompatible groups which inhibit or suppress in vivo metabolism of the peptide;
- J and each R are independently chosen from H, $C_{1-4}$ alkyl, $C_{1-4}$ alkenyl, $C_{1-4}$ alkynyl, $C_{1-4}$ alkoxyalkyl or $C_{1-4}$ hydroxyalkyl;

with the proviso that:
(i) when X is $CR_2$, then $Z^2$ is a metal complexing agent (L);
(ii) at least one of $R^1$ and $R^2$ bears at least one detectable moiety suitable for diagnostic imaging of the human body;
(iii) $R^1$ and $R^2$ include one or more of the peptide sequence consisting of NQEQVSPYTLLKG (SEQ ID NO: 2), which is a peptide fragment of $\alpha_2$-antiplasmin.

2. The compound of claim 1 where J is H.

3. The compound of claim 2 of formula:

$$Y-(CR_2)_x-(CH_2)_2CONH_2 \text{ or } Y-(CR_2)_y-(CH_2)_4NH_2$$

where x is an integer of value 0 to 4, and y is an integer of value 0 to 3.

4. The compound of claim 1 where at least one of $Z^1$ and $Z^2$ is a metal complexing agent.

5. The compound of claim 4 where $Z^2$ is a metal complexing agent and $Z^1$ is not a metal complexing agent.

6. A metal complex of the compound of claim 4.

7. The metal complex of claim 6 where the metal is a radiometal.

8. The radiometal complex of claim 7 where the radiometal is $^{99m}Tc$.

9. A preparation for human administration comprising the compound of claim 1.

10. A kit comprising the compound of claim 1 useful in the preparation of metal complexes.

* * * * *